US00PP09682P

United States Patent [19]

Bloom

[11] Patent Number: Plant 9,682

[45] Date of Patent: Nov. 5, 1996

[54] PERSICARIA PLANT NAMED TAURUS

[76] Inventor: Alan H. V. Bloom, Bressingham Hall, Bressingham, Diss, Norfolk, IP22 2AB, England

[21] Appl. No.: 499,253

[22] Filed: Jul. 7, 1995

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—Foley & Lardner

[57] ABSTRACT

A distinct cultivar of Persicaria plant named Taurus, characterized by its compact habit, deep crimson flowers which do not fade, long fall flowering which continues until severe frost, and its upright flowering spikes which make this cultivar ideal for borders or cut flowers.

2 Drawing Sheets

The present invention relates to a new and distinct cultivar of hardy perennial herbaceous plant of the genus Persicaria, botanically known as *Persicaria amplexicaulis,* and known by the cultivar name Taurus.

The new cultivar was discovered by the inventor in a display garden at Bressingham Hall, Bressingham, Diss, Norfolk, England, as a chance seedling. The origin is not certain, although plants of *Persicaria atrosanguineum* and plants of *Persicaria amplexicaulis* 'Firetail' were under cultivation nearby. The new cultivar was noted due to its deep crimson flowers, deeper in color than those of 'Firetail,' and which do not fade as the flowers of 'Firetail' and most other cultivars of the species do.

The first act of asexual reproduction was accomplished when vegetative cuttings were taken from the new cultivar by the inventor in a controlled environment at Bressingham. Examination of plants grown from these cuttings has demonstrated that the combination of characteristics as herein disclosed for Taurus are firmly fixed and are retained through successive generations of asexual reproduction.

Taurus is quite distinct from other forms of the species. It compares most closely to plants of the species *Persicaria atrosanguineum* and the cultivar 'Firetail,' both of which are considerably taller than Taurus by approximately 18 inches. It also flowers later in the fall than the comparison cultivars, with flowers of Taurus often continuing until severe frosts, typically late October to early November in Bressingham. These features, in combination with its deep crimson flowers which do not fade, uniquely distinguish the new cultivar.

The photographic drawings show a typical plant of the new cultivar, with the colors being as nearly true as possible with illustrations of this type.

The photograph on sheet 1 shows a plant of Taurus growing in a border setting.

The photograph on sheet 2 comprises a closeup view of a portion of a plant of Taurus, more clearly showing the stiff upright flowering spikes and the deep crimson flower color.

DETAILED PLANT DESCRIPTION

The following is a detailed description of Taurus, with color determinations and comparisons being based on The Royal Horticultural Society Colour Chart (R.H.S.).

Classification:

*Origin.*—Seedling.

*Parentage.*—*Persicaria amplexicaulis* 'Firetail'.

Plant:

*Habit.*—Clump forming.

*Size.*—Mature plants are over 70 cm (30 inches) in height with a spread of about 70 cm (30 inches).

*Root system.*—Rhizomatous.

*Plant vigor.*—A perennial that shows vigorous and healthy growth throughout Great Britain.

*Blooming habit.*—Spikes of minute single flowers produce 2–3 spikes per stem, carried above the foliage. The new cultivar is ideal for borders or for cut flowers.

*Blooming period.*—From mid-July until frost.

*Hardiness.*—Winter hardy throughout the British Isles. The plant has not been fully tested for maximum summer temperature tolerance above 32° C. (90° F.).

Foliage:

*Arrangement.*—Leaves are acuminate with pointed tip and cordate base.

*Type.*—Herbaceous.

*Texture.*—Both upper and lower surfaces are rough and dull.

*Shape.*—Entire.

*Length.*—10 cm.

*Width.*—5 cm.

*Colors.*—For mature leaves, upper and under surfaces are 138A.

*Petiole length.*—2 mm.

*Margins.*—Entire.

*Apex.*—Acute.

*Base.*—Cordate.

Flowers:

*Petal shape.*—Obtuse.

*Flower type.*—Spike.

*Flower size.*—7–8 cm long×1.5 cm diameter.

*Color.*—In mature flowers, petals are 47A.

*Stamens.*—4–8 small stamens.

It is claimed:

1. A new and distinct variety of Persicaria plant named Taurus, as shown and described.

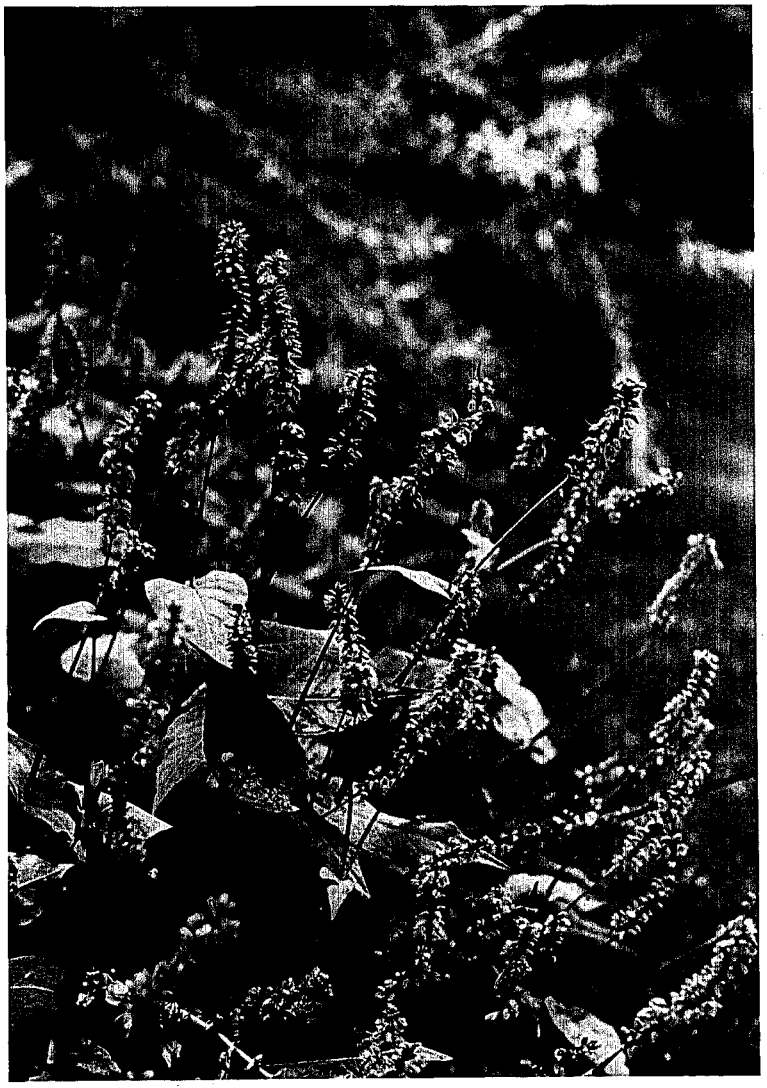

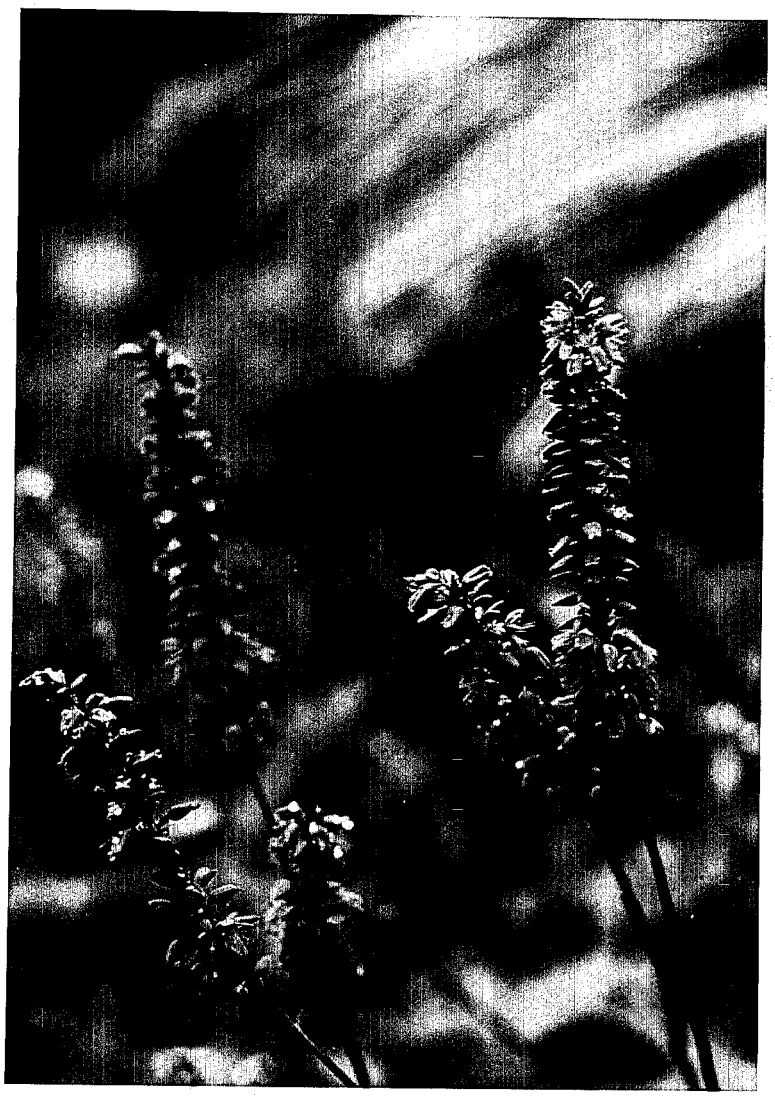

* * * * *